(12) United States Patent
Fujita

(10) Patent No.: US 9,045,726 B2
(45) Date of Patent: Jun. 2, 2015

(54) DEVICE FOR AUTOMATICALLY ANALYZING MICROORGANISMS AND METHOD FOR AUTOMATICALLY ANALYZING MICROORGANISMS

(75) Inventor: Hiroko Fujita, Takahagi (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 237 days.

(21) Appl. No.: 13/147,141

(22) PCT Filed: Jan. 13, 2010

(86) PCT No.: PCT/JP2010/000120
§ 371 (c)(1),
(2), (4) Date: Jul. 29, 2011

(87) PCT Pub. No.: WO2010/087110
PCT Pub. Date: Aug. 5, 2010

(65) Prior Publication Data
US 2012/0021449 A1      Jan. 26, 2012

(30) Foreign Application Priority Data

Jan. 29, 2009   (JP) ................................. 2009-017452

(51) Int. Cl.
*C12Q 1/02* (2006.01)
*C12M 1/34* (2006.01)

(52) U.S. Cl.
CPC ............... *C12M 41/36* (2013.01); *C12M 41/26* (2013.01)

(58) Field of Classification Search
None
See application file for complete search history.

(56) References Cited

U.S. PATENT DOCUMENTS

| | | | | |
|---|---|---|---|---|
| 4,829,005 A | * | 5/1989 | Friedman et al. | 435/288.1 |
| 4,956,297 A | | 9/1990 | Hood et al. | |
| 5,070,014 A | | 12/1991 | Dorn | |
| 7,297,531 B2 | * | 11/2007 | Goldman et al. | 435/288.2 |
| 7,521,210 B2 | | 4/2009 | Knudsen | |

FOREIGN PATENT DOCUMENTS

| | | |
|---|---|---|
| JP | 59-102399 | 6/1984 |
| JP | 02-245174 | 9/1990 |
| JP | 06-070794 | 3/1994 |
| JP | 10-084942 | 4/1998 |
| JP | 11-225742 | 8/1999 |
| JP | 2994675 | 10/1999 |
| JP | 2007-508003 | 4/2007 |
| WO | WO 2005/035748 A1 | 4/2005 |

OTHER PUBLICATIONS

Desai et al., 2003. Separation, Identification and Characterization of Microorganisms by Capillary Electrophoresis. Microbiology and Molecular Biology Reviews, vol. 67, No. 1, pp. 38-51.*
Hazen, 1995. New and emerging yeast pathogens. Clinical Microbiology Reviews, vol. 8, No. 4, pp. 462-479.*
Weinstein, 1996. Current Blood Culture Methods and Systems: Clinical Concepts, Technology and Interpretation of Results. Clinical Infectious Diseases, vol. 23, pp. 40-46.*
Price et al. 1994. Fluconazole Susceptibilities of *Candida* Species and Distribution of Species Recovered from Blood Cultures over a 5-Year Period. Antimicrobial Agents and Chemotherapy, vol. 38, pp. 1422-1424.*
BBL™. Prepared Turbidity Standard, CE 8808421JAA Feb. 2005 © 2005 BD, pp. 1-3.*
IGEM:Caltech/2007/Protocols/Ecoli liquid cultureGNU FDL or Creative Commons BY-SA 2007.*
Extended European Search Report issued in European Patent Application No. EP 10735582.8 dated Aug. 7, 2013.
Nagai et al., "A Microfluidic Device to Control Bio Actuators of Microorganisms, An Application to *Vorticella convallaria*," Solid-State Sensors, Actuators, and Microsystems: Conference, Jun. 2009, Transducers 2009.

* cited by examiner

*Primary Examiner* — Jon P Weber
*Assistant Examiner* — Kailash C Srivastava
(74) *Attorney, Agent, or Firm* — McDermott Will & Emery LLP

(57) ABSTRACT

After culturing blood, a culture liquid determined as positive is transplanted into a plate medium and a bacterial cell suspension that is directly usable for identifying and testing antibiotics-sensitivity is prepared without forming colonies. Provided are a device for automatically analyzing microorganisms and a method therefor whereby blood culture and an identification and antibiotics-sensitivity test can be continuously operated. A device for automatically analyzing microorganisms which is configured so that a blood culture test and an identification and antibiotics-sensitivity test can be automatically and continuously conducted, wherein means for pretreating a cultured blood sample comprises a mechanism for removing culture liquid components in the course of the blood culture and a mechanism for controlling the microbial concentration (bacterial cell count) to a constant level after the blood culture.

6 Claims, 2 Drawing Sheets

DEVICE FOR AUTOMATICALLY ANALYZING MICROORGANISMS AND METHOD FOR AUTOMATICALLY ANALYZING MICROORGANISMS

RELATED APPLICATIONS

This application is the U.S. National Phase under 35 U.S.C. §371 of International Application No. PCT/JP2010/000120, filed on Jan. 13, 2010, which in turn claims the benefit of Japanese Application No. 2009-017452, filed on Jan. 29, 2009, the disclosures of which Applications are incorporated by reference herein.

TECHNICAL FIELD

The present invention relates to a device for automatically analyzing microorganisms and a method therefor, and particularly relates to a device for automatically analyzing microorganisms and a method therefor which continuously conduct a blood culture test and an identification and antibiotics-sensitivity test without an isolation culture; significantly shorten time (days) leading up to a result report; and have an improved effect to achieve a next day's report.

BACKGROUND ART

A blood culture test is an important test in a microorganism test. To rapidly detect bacteria and fungus from blood, which is originally germ-free, is very important for diagnosing blood sepsis and bacteremia, which are serious infections. On the other hand, an appropriate antibiotic therapy needs to identify species of microorganisms, to rapidly measure sensitivity to an antibiotic, to determine a type of an effective antibiotics and its concentration, and to decide on courses of treatment.

Conventional flow of a blood culture test in a laboratory is as follows. Collected blood is cultured in a device for blood culture test. After the test is determined as positive, a sample is taken out from a cultural bottle and the sample is applied to a culture medium. After a culture for several hours to one night (an isolation culture), a bacteria suspension is prepared by picking from formed colonies. Then, the bacteria suspension is inoculated into a measuring device of a device for identification and antibiotics-sensitivity test. In other words, after testing with the device for blood culture test, culture is conducted from several hours to one night, and then the test is conducted by using other device for identification and antibiotics-sensitivity test.

Usually, since sepsis and bacteremia are serious illness, types of bacteria and a type and concentration of antibiotic which is effective for the bacteria is required as soon as possible. However, since a period to be positive is previously not known, time lag (spare time) is often generated. Consequently, the sample cannot be smoothly transferred into the identification and sensitivity test, which is a next process. Particularly, when a test result of blood culture is determined as positive in the nighttime, the laboratory is unattended in many cases. Consequently, transplant to subculture (isolation culture) is conducted after the operation in the laboratory starts next morning. Therefore, inoculation to the device for the identification and sensitivity test delays, and a report of the result of the identification of the microorganisms and the result of the antibiotics sensitivity finally delays, unable to decide appropriate courses of treatment at an early stage. Practically, for serious illness, such as sepsis and bacteremia, existence or nonexistence of bacteria is more important than a type of the bacteria. Therefore, the fact is that, when the test of a blood culture is determined as positive, an antibacterial antibiotic which has a wide range of antibacterial spectrum is administered by a medical doctor not waiting for the result of the antibiotics-sensitivity test. Such medication is one of the reasons for emergence of antibiotics resistance bacteria, which becomes a problem in these years.

Although attempts for shorting a period of time leading up to the test result report and for laborsaving have been made, a significant effect is not obtained because there are many technological problems. Even if technological problems are solved, the laboratory cannot be operated for 24 hours because a person links operations for two devices for the blood culture test and the identification and sensitivity test. In large majority of the laboratory site except a part of institutions, loss of time is generated in an actual condition. As a result, four days or more has been spent leading up to the result report.

In order to shorten time and to save labor, for example, an example is shown in a method described in Patent Literature 1 in which a constant quantity of bacteria can be collected using a simple bar with grooves. In a method described in Patent Literature 2, an example is shown of a bottle which is effective for inoculating a bacterial cell suspension to a device after controlling the concentration. Unfortunately, even if these methods are employed, laborsaving being achieved and devices being not linked, it is difficult to greatly contribute to shortening the final report time. In addition, although the bar or the bottle is excellent for the operation by a person, these tools are not appropriate for automation using devices because of the complex steps.

PRIOR ART DOCUMENTS

Patent Literatures

Patent Literature 1: Japanese Patent No. 2994675
Patent Literature 2: Japanese Patent Application Publication Hei 11-225742

SUMMARY OF INVENTION

Technical Problem to be Solved

A problem to be solved by the present invention is, after culturing blood, a sample determined as positive is transplanted and an isolation culture is conducted for one night without forming colonies; the sample being transferred to an identification and sensitivity test without any treatment; a period of time required to report the result of the identification and antibiotics-sensitivity test being shortened; and the result being possible to report next day. However, under the existing circumstances, when a culture liquid in a bottle which indicates positive in blood culture is used and the culture liquid is directly inoculated to a device for measuring and culturing of the device for identification and sensitivity test, there are problems in which correct results are not obtained because components in the blood culture bottle affect antibiotics contained in the device for measuring and culturing of the device for identification and sensitivity test and in which pH of the sample which is changed during the blood culture affects to the identification and sensitivity test. In the identification and sensitivity test, it is essential that a quantity of bacteria of the inoculation to the device for measuring and culturing is set to a predetermined concentration. However, in order to remove the effect of antibiotic antibiotics administered for a patient, activated charcoal and the like are previously added to the blood culture bottle. Consequently, bacteria concentration is difficult to measure by cloudiness. In actual condition, since an effect of coloring caused by blood cells included in blood also exists, optical measurement is difficult to conduct. In addition, quantity of bacteria (bacteria concentration) is insufficient without any treatment in many cases, so that the quantity of the bacteria should be increased up to the certain bacterial cell count.

An object of the present invention is to provide a device for testing bacteria and a method therefor in which, by solving the above-described problems, a sample is transferred to an identification and sensitivity measurement, without an isolation culture by transplant, to significantly shorten test time and to make the report next day. Another object of the present invention is to provide a method for testing bacteria and a device therefor which take account of countermeasures against biohazard, such as infection, by automatically connecting the blood culture test to the identification and antibiotics-sensitivity test without intervention of a person.

Solution to Problem

The above-described problems can be solved by providing a device which includes a mechanism for pretreating a sample collected from a positive bottle after the blood culture. More specifically, these problems can be solved by providing a mechanism for filtering a positive sample, a mechanism for controlling pH of the sample, a mechanism for concentrating the bacterial cell count in the sample to predetermined concentration, and a mechanism for obtaining predetermined quantity of a bacterial cell suspension by inoculating bacteria in the sample to a liquid culture medium.

Advantageous Effect of Invention

In a method of the present invention, components in the culture liquid of the blood culture can be removed by the mechanism for filtering the sample after the blood culture is determined as positive. In other words, activated charcoal, an ion-adsorption resin and other components are included in a blood culture bottle in some cases in order to adsorb an administered antibiotic contained in the blood of a patient specimen already in chemotherapy. By removing these components, an effect to antibiotics used for an identification and sensitivity test can be removed. In the identification and sensitivity test, it is essential to keep the inoculation quantity of bacteria to a device constant in predetermined concentration correctly and in good repeatability. At this time, there are problems in which culture liquid is colored and clouded by the activated charcoal, the ion-adsorption resin, blood cells, and other components, unable to properly control a bacterial cell suspension. However, the culture liquid can optically be measured by filtering. Additionally, pH of the culture liquid is lowered by carbon dioxide metabolized and produced with growth of microorganisms in the blood culture.

In the present invention, pH of the culture liquid is returned to an appropriate range by the mechanism for adding a pH controlling reagent and thereby an effect to a reagent for test and measurement of identification and sensitivity can be removed. In order to obtain a correct result in the identification and sensitivity test, a bacterial cell suspension having a certain concentration is needed to be inoculated into a device for measurement. However, the quantity of bacteria (bacteria concentration) is insufficient in many cases when the bacterial cell count in the blood culture bottle is not changed, unable to use the sample in the device for identification and sensitivity test without any treatment. Therefore, in the present invention, in order to obtain a bacterial cell suspension having a concentration of certain bacterial cell count or more, a positive bottle is centrifuged and sediment is put in normal saline solution or special test solution. The bacterial cell suspension having a certain concentration can be obtained with a configuration to collect the bacteria by further centrifuging, if necessary. The bacterial cell suspension can be concentrated by using an ultrafilter membrane and the like. When a concentration of the bacterial cell suspension does not reach a predetermined concentration, a bacterial cell suspension having a predetermined bacteria concentration can be obtained by inoculating a small amount of concentrated bacterial cell suspension which is collected by centrifuging the bottle into a new liquid culture medium and by culturing the concentrated bacterial cell suspension in a short period.

Loss of time can be removed and required time for entire test can be shortened by automatically transferring a sample to an identification and antibiotics-sensitivity test without forming colonies by subculture after the blood culture, as described above. Laborsaving is also achieved by providing a fully automatic device. This method is also applicable without any difficulty to the test at a time when the laboratory is unattended, such as nighttime and holidays. The test, which usually requires 4 days or more, can be shortened by at least 2 days or more. Integration of microorganism tests in one device has an advantage that cost to produce the device, cost to run the device, and expansion of special space are eliminated. Test operation taking account of safety from a viewpoint of biohazard countermeasures is possible by conducting a series of test flow leading up to a result report without intervention of a person.

DESCRIPTION OF EMBODIMENTS

A device for microorganism test and a method therefor are attained, by providing mechanisms for pretreating a culture liquid after a determination of blood culture as positive, in which the sample is automatically transferred to an identification and sensitivity test without forming colonies in a plate medium after the determination of blood culture as positive, resulting in significant reduce of required time to obtain a result report of the identification and sensitivity test.

Hereinafter, embodiments of the present invention are described using the drawings.

First Embodiment

Figure 1:
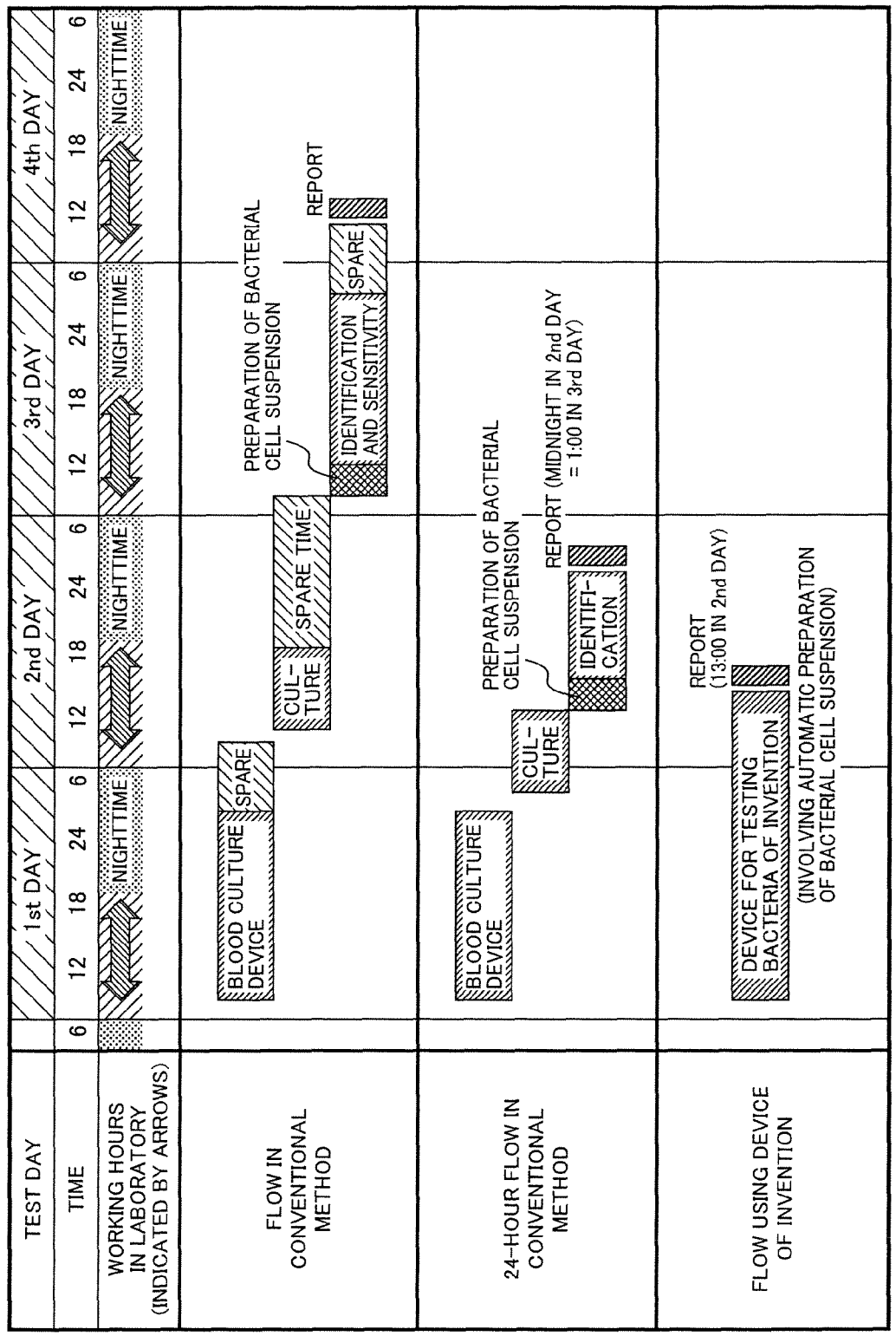
FIG. 1 is a chart comparing flows and time leading up to a test result report between a conventional method and a method using a device of the present invention.

FIG. 1 shows workflows of a test using a device of the present invention and a conventional device.

It is assumed that blood, which is a patient specimen, arrives at 9 o'clock of the first day. Laboratory staff immediately sets the blood in a device for culturing blood and starts culture. Usually, the culture is continuously monitored from 5 days to 7 days and 90 percents of samples are determined as positive from 1 day to 2 days. In this case, the blood is cultured for 18 hours and the result is determined as positive at 3 o'clock in the night. However, the positive test blood is placed in the device for culturing blood without any treatment because the laboratory is unattended late at night. At 8 o'clock in the morning of the second day, operations of the laboratory start. At 9 o'clock, the sample containing the blood is applied to a plate culture medium from the positive bottle, and then the sample is cultured in a thermostatic oven from 10 o'clock. This process is isolation culture of transplant. Colonies are observed on the culture medium 8 hours or more at the earliest, that is, after 18 o'clock in the evening.

However, that time is already off duty for test operation, and the sample is continued to be cultured in the thermostatic oven until next morning. At 8 o'clock in the third day, bacteria of the colony on the culture medium are picked by the laboratory staff. The picked sample is suspended in normal saline solution, turbidity of the sample being controlled, and then the controlled sample being tested by the device for measuring the identification and sensitivity. The picking to the control of the bacterial cell suspension is usually conducted in the morning. The sample is set to the device at 12 o'clock in the afternoon, and then the result is usually obtained from 8 hours to 10 hours later. At this time, it is 8 o'clock to 10 o'clock at night of the third day. Although the result of the identification and sensitivity is obtained, it is off duty time for the test operation. Consequently, the report of the result to a medical doctor is 8 o'clock in the morning of next day, which is the fourth day. This is a conventional flow. This flow is not applicable for a serious patient, so that operation in the laboratory is conducted for 24 hours and the laboratory staff works during nighttime. This is the next flow. A specimen arrives at 9 o'clock in the first day, and determination as positive is made at 3 o'clock in the night. The sample is immediately applied to a plate medium and the isolation culture starts from 4 o'clock.

After 8 hours, colonies are formed at noon of the second day. An operation for preparing the bacterial cell suspension is conducted for 3 hours, and the obtained sample is set to the device for measuring the identification and sensitivity at 3 o'clock in the afternoon of the second day. Determination after 9 hours is made at 12 o'clock late at night, that is 0 o'clock of the third day. If a medical doctor is ready, medication information is imparted to the patient in a period of time from the late night to the early morning of the third day at the earliest.

On the other hand, the flow in the case of the present invention is as follows. A specimen arrives at 9 o'clock in the first day, and determination as positive is made at 3 o'clock in the night. A sample from a positive bottle is not applied to a plate. Pretreatment of the sample, such as filtration and pH control, is automatically operated in a device. Time required to prepare a bacterial cell suspension is no more than 1 hour. If the sample is set to the device for identification and sensitivity at 4 o'clock in the early morning, the measurement result can be reported to the medical doctor after 9 hours, that is, at 13 o'clock of the second day. The time can be shortened for 2 days or more.

Figure 2:
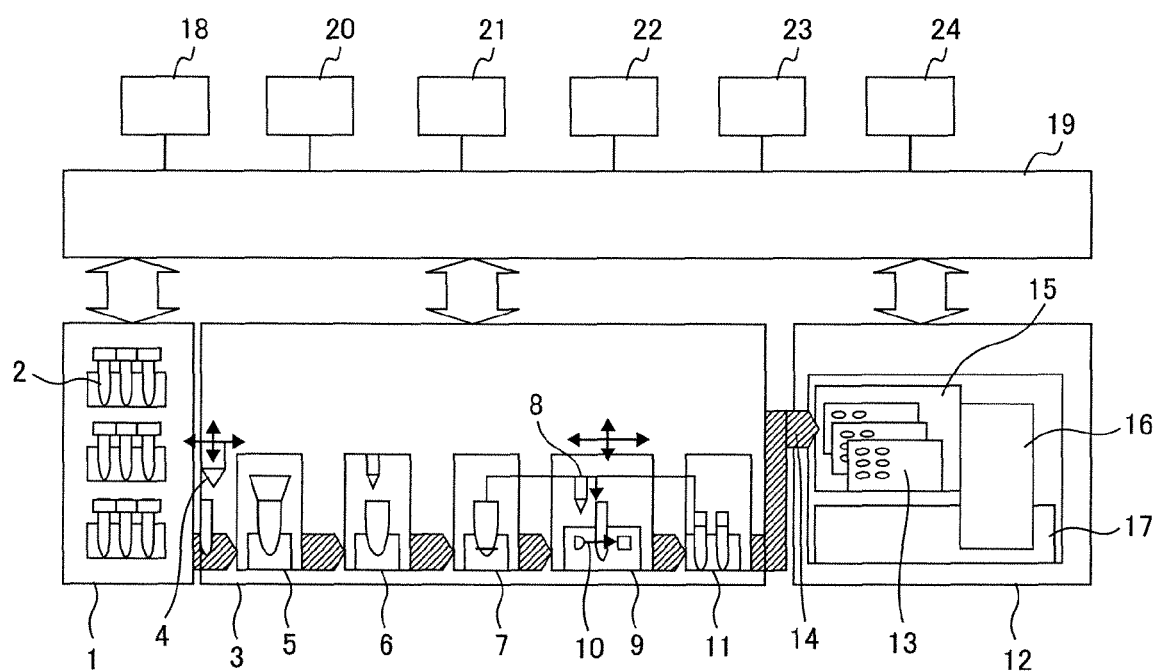
FIG. 2 is a view showing an operating principle of an automatically analyzing device in accordance with an embodiment of the present invention.

FIG. 2 is a view showing a principle of a device for automatically analyzing microorganisms. In FIG. 2, 1 represents a blood culture unit. In the blood culture unit 1, many blood culture bottles 2, for example 60 bottles, can be placed. The blood culture unit 1 is maintained at a predetermined temperature. 3 represents entire pretreatment unit. The pretreatment unit 3 includes a filtering mechanism 5, a pH controlling mechanism 6, a centrifugation unit 7, a bacterial cell suspension controlling unit 9, and a liquid culture unit 11. 12 represents a unit for analyzing identification and antibiotics-sensitivity. The bacterial cell suspension controlled through the pretreatment unit 3 is filled into a device for culturing and measuring 13 by an inoculation mechanism 14. In the device, a number of antibiotics having different concentrations and types or a number of different types of nutrient medium for identifying a type of bacteria are filled. The device is maintained in a constant temperature in a culturing unit 15 and the inoculated microorganisms are cultured. The device 13 is withdrawn from the culturing unit by a conveying unit 16 in constant time intervals and is optically measured by a detection unit 17.

18 represents a microcomputer. 19 represents an interface. 20 represents a log converter and an A/D converter. 21 represents a printer. 22 represents a CRT. 23 represents a hard disk as a memory device. 24 represents an operation panel.

In the above-described configuration, an operator inputs information of analysis request using the operation panel 24. The input information of analysis request is stored in a memory in the microcomputer 18. The blood sample, which is poured into the blood culture container 2 and set to a predetermined place in the blood culture unit 1, is cultured for a given time. With growth of the microorganisms contained in the blood, metabolized substances, such as carbon dioxide, are produced and pH of the culture medium is changed. This change is detected by a pH sensor. Measurement is conducted in constant time intervals. Determination as positive or negative is made by the microcomputer 18 using a predetermined algorithm. A constant quantity of the culture liquid determined as positive in the blood culture container 2 is taken by a nozzle 4 for aliquoting.

After this, the sample is, not applied to a plate medium and cultured as a conventional method, pretreated in the pretreatment unit 3 and the bacterial cell suspension is prepared. However, microorganisms in the blood should be single species. When chemotherapy is already conducted, in order to remove an effect of administered antibiotics, a culture medium is often used to which activated charcoal or cation exchange and non-ionic adsorption resin is added as an adsorbent. Therefore, there is a problem that the bacterial cell suspension can not be prepared in a correct bacterial cell count (a quantity of bacteria) because, when a culture liquid after the blood culture is used for a sample for preparing a bacterial cell suspension without any treatment, carbon particles soar because the particles are fine, and coloring or turbidity affects the control of the bacterial cell suspension. Consequently, by removing disturbance components using the filtering mechanism 5, a sample having correct concentration of bacteria can be provided to an identification and sensitivity test. Other than carbon particles, blood cell components also disturb the correct control of the bacterial cell suspension. It is preferred that the filter have pores of about 0.2 micrometer to several micrometers, which can pass the microorganism and remove the carbon particles, the ion-adsorption resin, and the blood cell components.

6 is a pH controlling mechanism, which is equipped with a pH controlling reagent. By adding the reagent to the culture liquid after the blood culture, a pH of the culture liquid which is lowered by carbon dioxide metabolized and produced with growth of microorganisms is controlled and an effect to reactivity of the identification test can be removed. In a test for identifying microorganisms or for measuring sensitivity to antibiotics, a bacterial cell suspension having a predetermined and correct quantity of bacteria (concentration) is required. This is because a correct result is not obtained when the quantity of bacteria is insufficient or excessive. 7 represents the centrifugation unit. In many cases, a bacteria concentration does not reach a constant number for microorganisms in a culture medium which is determined as positive in blood culture.

Consequently, a culture liquid after the blood culture is centrifuged to obtain sediment containing the microorganisms. Removal of the blood cell components, the carbon particles, and the ion-adsorption resin, which are described above, may be conducted by this centrifugation process. The sediment is taken by a bacteria collection mechanism 8 and is dissolved in normal saline solution or special test solution in the bacterial cell suspension controlling unit 9. The bacterial cell suspension in the normal saline solution is optically measured by a photometer 10. As for an optical system, various methods, such as measuring absorption, turbidity, and scattering light, can be used as long as degree of cloudiness of a suspension of microorganisms can be measured. Usually, the sample is desirably prepared to be $5\times10^5$ CFU/mL as a result of a series of dilution.

When a bacterial cell suspension with low concentration does not satisfy a predetermined concentration of bacterial cell suspensions, the bacterial cell suspension may automatically be inoculated to a new liquid culture medium in the liquid culture unit 11 to increase the bacteria. The liquid culture unit 11 is maintained in a constant temperature and can supply samples having a sufficient bacterial cell count and bacteria concentration by a culture within 12 hours in many cases. A shaking culture may be conducted in order to shorten culture time. The bacterial cell suspension during the liquid culture is automatically taken by the bacteria collection mechanism 8 after the growth is confirmed by a growth monitor (not shown in FIG. 2). The bacterial cell suspension remains in the liquid culture medium or is dissolved in normal saline solution or special test solution in the bacterial cell suspension controlling unit 9, then being optically measured by the photometer 10 to be prepared $5\times10^5$ CFU/mL. When a process for increasing the bacteria is added in the way described above, time to final result can be shortened for at least 8 to 12 hours compared to a conventional method which generates colonies because the sample is automatically transferred to subculture with liquid culture soon after the blood culture is determined as positive.

The bacterial cell suspension prepared in $5\times10^5$ CFU/mL is filled in the device for culturing and measuring 13 in the unit for analyzing identification and antibiotics-sensitivity 13 by the inoculation mechanism 14, and is maintained at constant temperature and cultured in the culturing unit 15.

When various antibiotics, which are previously filled in the device and have different types and concentrations, have an antibacterial effect to microorganisms, the bacterial cell suspension does not become cloudy. When the antibiotics do not have the effect, the suspension becomes cloudy by growth of microorganisms. This minimum inhibitory concentration is MIC and is reported to the clinic staff. In a manual test, the antibacterial effect is usually determined after a culture for one night (18 hours). How to obtain this result in a short period of time is the most important point for rapid diagnosis. The device 13 is withdrawn from the culturing unit by the conveying unit 16 in constant time intervals and is optically measured in constant intervals. The measured optical signals are loaded to the microcomputer 18 through the logarithmic converter, an A/D converter 20, and the interface 19. More specifically, cloudiness of bacteria growth is detected in high sensitivity by the optical system in the detection unit 17, and rise of growth is determined by the predetermined algorithm in the microcomputer 18, so that result determination can be rapidly obtained.

The mechanism of the pretreatment unit in the present invention may be used partially if necessary. Effective result also can be obtained when the entire unit is used. The sequence of the units is not fixed, and any pretreatment may preferentially be conducted. For example, the liquid culture unit may be used before the filtering unit.

Second Embodiment

In the first embodiment, in order to collect microorganisms in a culture liquid which is pretreated by filtering and pH control, the microorganisms also can be obtained by concentrating a bacteria concentration using an ultrafilter membrane. This method is to keep only essential components and to discharge unnecessary solvent and water like a dialysis tube. After sufficient concentration is obtained, a liquid with suspending bacteria may be controlled. It is also effective to combine centrifugation in order to enhance efficiency.

EXPLANATIONS OF REFERENCE NUMERALS

1 blood culture unit
2 blood culture bottle
3 pretreatment unit
4 nozzle for aliquoting
5 filtering mechanism
6 ph controlling mechanism
7 centrifugation unit
8 bacteria collection mechanism
9 bacterial cell suspension controlling unit
10 photometer
11 liquid culture unit
12 unit for analyzing identification and antibiotics-sensitivity
13 device for culturing and measuring
14 inoculation mechanism
15 culturing unit
16 conveying unit
17 detection unit
18 microcomputer
19 interface
20 log converter and A/D converter
21 printer
22 CRT
23 hard disk
24 operation panel

The invention claimed is:

1. A method for automatically analyzing microorganisms, comprising the steps of:
   (a) culturing blood in a blood culture medium, the blood culture medium comprising a component that includes at least one of activated charcoal, carbon particles and an adsorption resin;
   (b) after the step (a), detecting growth of microorganisms in the blood culture medium by an optical detection mechanism, wherein the optical detection mechanism detects cloudiness of the blood culture medium or metabolized substances produced by the microorganisms;
   (c) subjecting an aliquot of the blood in the blood culture medium, in which the growth of the microorganisms is detected, to a first pretreatment, the first pretreatment comprising filtering the aliquot of the blood culture medium by a filter to remove the components and blood cell components from the aliquot of the blood culture medium such that the microorganisms pass through the filter;
   (d) subjecting the pretreated aliquot of the blood culture medium of step (c) to a second pretreatment, the second pretreatment comprising preparing a cell suspension sample having a predetermined concentration of the microorganisms suitable for step (e), wherein the cell suspension sample is further cultured in a new liquid culture medium if the microorganism concentration of said cell suspension sample does not reach a predetermined concentration suitable for step (e); and (e) culturing said cell suspension sample in a culture container or a measurement container and conducting identification and antibiotics-sensitivity test of the microorganisms; wherein the identification and antibiotics-sensitivity test comprises detecting growth of the microorganisms in the culture container or the measurement container in presence of an antibiotic; and wherein the steps (a) to (e) are carried out automatically and continuously, wherein removing the effect of the blood culture in the step (c) further comprises adjusting pH of the aliquot of the blood culture medium.

2. The method according to claim 1, wherein the second pretreatment comprises centrifugation of the pretreated aliquot of the blood culture medium of step (c), sedimentation of the microorganisms and suspension of microorganisms in normal saline solution or special test solution to prepare the cell suspension sample.

3. The method according to claim 1, wherein the microorganisms include bacteria, and the cell suspension sample comprises a constant bacterial cell count.

4. The method according to claim 1, wherein the second pretreatment step further comprises monitoring the microorganisms concentration of the cell suspension sample by optical means.

5. The method according to claim 4, wherein the optical means is a photometer measuring absorption, scattering light, turbidity, or fluorescence.

6. The method according to claim 1, wherein the cell suspension sample having a predetermined concentration suitable for step (e) is prepared in normal saline solution or test solution.

* * * * *